United States Patent
Fallon et al.

(10) Patent No.: US 10,849,783 B2
(45) Date of Patent: Dec. 1, 2020

(54) FULL MOVEMENT JAW ADVANCEMENT ORAL APPLIANCE TO REDUCE THE EFFECTS OF SNORING AND/OR SLEEP APNEA

(71) Applicants: James S Fallon, Laguna Niguel, CA (US); Richard Jung, Laguna Niguel, CA (US)

(72) Inventors: James S Fallon, Laguna Niguel, CA (US); Richard Jung, Laguna Niguel, CA (US)

(73) Assignee: James S. Fallon

( * ) Notice: Subject to any disclaimer, the term of this patent is extended or adjusted under 35 U.S.C. 154(b) by 326 days.

(21) Appl. No.: 15/872,881

(22) Filed: Jan. 16, 2018

(65) Prior Publication Data
US 2019/0216632 A1    Jul. 18, 2019

(51) Int. Cl.
*A61F 5/56* (2006.01)
*A61C 7/36* (2006.01)

(52) U.S. Cl.
CPC .............. *A61F 5/566* (2013.01); *A61C 7/36* (2013.01)

(58) Field of Classification Search
CPC .............. A61F 2005/563; A61F 5/0003; A61F 5/0006; A61F 5/566; A61F 5/56; A61C 7/08; A61C 7/10; A61C 7/00; A61C 5/007; A61C 7/007; A83B 71/085
USPC ........................................................ 128/848
See application file for complete search history.

(56) References Cited

U.S. PATENT DOCUMENTS

| | | | |
|---|---|---|---|
| 5,868,138 A * | 2/1999 | Halstrom | A61F 5/566 128/848 |
| 8,833,374 B2 | 9/2014 | Fallon | |
| 10,383,758 B1 * | 8/2019 | Greenburg | A61F 5/566 |
| 2007/0292819 A1 * | 12/2007 | Scarberry | A61F 5/566 433/140 |
| 2008/0072915 A1 * | 3/2008 | Nelissen | A61F 5/566 128/848 |
| 2011/0030704 A1 * | 2/2011 | Hanna | A61C 7/08 128/861 |
| 2012/0145166 A1 * | 6/2012 | Fallon | A61F 5/566 128/848 |
| 2014/0120489 A1 * | 5/2014 | Klein | A61C 7/36 433/6 |
| 2015/0282900 A1 * | 10/2015 | Lee | A61C 7/36 433/19 |

(Continued)

*Primary Examiner* — Alireza Nia
*Assistant Examiner* — Kevin S Albers
(74) *Attorney, Agent, or Firm* — Morland C. Fischer

(57) ABSTRACT

Disclosed is a full movement jaw advancement oral appliance that is worn in the mouth of a user to reduce the effects of snoring and/or sleep apnea. The oral appliance includes an upper arch tray assembly against which the user's upper teeth carried are received, a lower arch tray assembly against which the user's lower teeth are received, and an intermediate guide post support tray that is connected at the bottom thereof to the lower arch tray assembly and at the top thereof to the upper arch tray assembly by an upper arch tray retaining post that extends therebetween. The upper arch tray assembly is movable in both horizontal and vertical directions relative to the lower arch tray assembly so that the positions of the user's upper and lower jaws can be adjusted relative to one another and the upper arch tray assembly will remain in receipt of the user's upper teeth when he opens his mouth during sleep.

6 Claims, 5 Drawing Sheets

(56) References Cited

U.S. PATENT DOCUMENTS

| | | | |
|---|---|---|---|
| 2015/0290025 A1* | 10/2015 | Valdemira | A61F 5/566 |
| | | | 128/848 |
| 2018/0036165 A1* | 2/2018 | Fallon | A61F 5/566 |
| 2018/0207021 A1* | 7/2018 | Newby | A61F 5/566 |
| 2018/0353321 A1* | 12/2018 | Veis | A61F 5/566 |
| 2018/0360646 A1* | 12/2018 | Bedford | A61F 5/566 |

* cited by examiner

FULL MOVEMENT JAW ADVANCEMENT ORAL APPLIANCE TO REDUCE THE EFFECTS OF SNORING AND/OR SLEEP APNEA

BACKGROUND OF THE INVENTION

1. Field of the Invention

This invention relates to a full movement jaw advancement oral appliance to be worn in the mouth and over the teeth of a user during sleep to reduce the effects of snoring and/or sleep apnea. The jaw advancement oral appliance includes upper and lower arch tray assemblies against which the user's upper and lower sets of teeth are positioned and wherein the upper arch tray assembly is adapted to move in both vertical and horizontal directions relative to the lower arch tray assembly in order to remain in receipt of the user's upper set of teeth should he open his mouth while at sleep and to adjust the position of the user's upper and lower jaws relative to one another to maintain an open airway to the user's throat.

2. Background Art

U.S. Pat. No. 8,833,374 issued Sep. 16, 2014 and entitled INTRA-ORAL MANDIBULAR ADVANCEMENT APPLIANCE describes a unique oral appliance to be inserted in the mouth and worn over and against the teeth of a user to maintain an open airway through the appliance to the user's throat and thereby improve the user's breathing during sleep. The patented oral appliance has particular application for use by those wishing to reduce the effects of snoring and/or sleep apnea. The appliance includes upper and lower tray assemblies against which the user's upper and lower sets of teeth are seated during use. The lower tray assembly is slidably adjustable in a horizontal direction relative to the upper tray assembly to correspondingly and selectively adjust the position of the user's lower jaw relative to his upper jaw in order to keep the aforementioned airway open as the user's condition changes over time.

Depending upon how the user sleeps and moves about, the position of the patented oral appliance could shift in the user's mouth relative to his upper and lower sets of teeth. In particular, if the user were to open his mouth while at sleep, the appliance could separate from his upper set of teeth. In this case, when the user closes his mouth, the appliance may be out of alignment with his upper set of teeth which could reduce the effectiveness of the appliance. What would therefore be desirable is an improved full movement jaw advancement oral appliance similar to that described above, but having a unique structural configuration by which to also enable the oral appliance to remain in place over and against the user's teeth throughout the night whether the user's mouth is open or closed so that an open airway is maintained.

SUMMARY OF THE INVENTION

In general terms, a full movement jaw advancement oral appliance is disclosed to be worn in the mouth and over the teeth of a user during sleep to reduce the effects of snoring and/or sleep apnea. The oral appliance includes flexible upper and lower arch tray assemblies which are engaged by the user's upper and lower sets of teeth during sleep. Each of the upper and lower arch tray assemblies includes a relatively soft and impressionable tooth impression liner against which the user's upper and lower sets of teeth are pressed and a relatively hard liner receiving tray to which a tooth impression liner is bonded.

The lower arch tray assembly of the oral appliance includes an intermediate guide post support tray having an upper arch tray retaining post standing vertically upward from the front thereof. A stop extends outwardly from the top of the retaining post. A retaining post receiving opening is formed in the front of the liner receiving tray of the upper arch tray assembly so as to lie in axial alignment with the upstanding upper arch tray retaining post. The upper and lower arch tray assemblies are coupled together so as to lie one above the other when the retaining post carried by the intermediate guide post receiving tray is pushed through the retaining post receiving opening. By virtue of the foregoing, when the user of the full movement oral appliance opens and closes his mouth during sleep, the upper arch tray assembly will move up and down along the upper arch tray retaining post through a vertical plane relative to the lower arch tray assembly. Thus, the user's upper set of teeth will remain in receipt by and avoid being separated from the tooth impression liner of the upper arch tray assembly. In this case, the oral appliance will remain in alignment with the user's teeth so as to preserve the effectiveness thereof and thereby maintain the open airway therethrough to the user's throat.

A pair of position control blocks are located on top and at opposite sides of the liner receiving tray of the lower arch tray assembly for slidable receipt within respective locking channels that are formed at opposite sides of the adjacent bottom of the intermediate guide post support tray. Each of the position adjustment blocks and the locking channels has a set of teeth which run along one side thereof to be moved into mating engagement with one another so as to hold the position adjustment blocks within the locking channels and thereby lock the upper arch tray assembly in place relative to the lower arch tray assembly.

When it is desirable to displace the upper arch tray assembly of the full movement jaw advancement oral appliance through a horizontal plane relative to the lower arch tray assembly so that the user's upper jaw can be repositioned relative to his lower jaw, squeezing forces are momentarily applied in opposite directions to the opposite sides of the intermediate guide post support tray of the lower arch tray assembly. As a result of the squeezing forces, the guide post support tray is temporarily compressed such that the teeth at one side of the locking channels thereof are moved out of their former mating engagement with the teeth at one side of the position adjustment blocks of the liner receiving tray of the lower arch tray assembly. A pushing force is now applied to the guide post support tray to cause the locking channels thereof to move axially relative to the position adjustment blocks. At the same time, the tooth impression liner and the liner receiving tray of the upper arch tray assembly which are coupled to the guide post support tray by the upper arch tray retaining post will move with the guide post support tray to adjust the location of the upper arch tray assembly and the user's upper jaw relative to the lower arch tray assembly and the user's lower jaw. Once the position of the upper arch tray assembly and the user's upper jaw has been adjusted as necessary to meet the needs of the user, the momentary squeezing forces being applied to the guide post support tray are terminated. Accordingly, the guide post support tray will now automatically expand back to its original shape, whereby the teeth of the locking channels will move back into their mating engagement with the position adjustment blocks to once again hold the upper and lower arch tray assemblies in place one above the other.

DESCRIPTION OF THE PREFERRED EMBODIMENT

Figure 1:
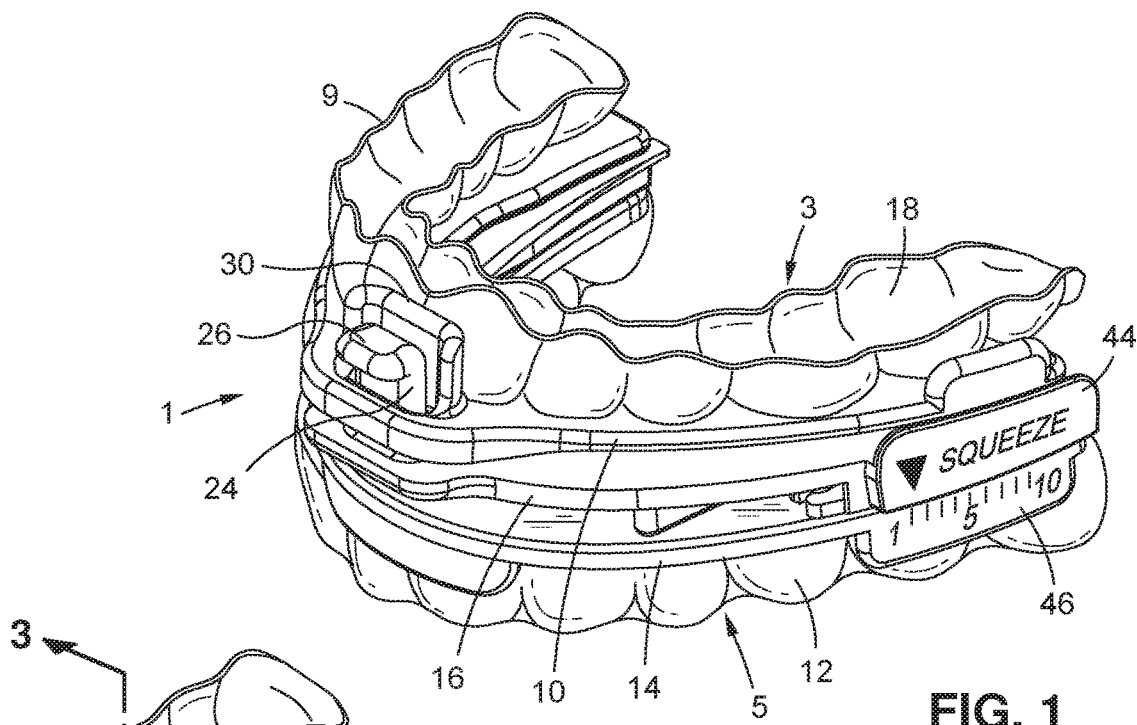
FIG. 1 is a perspective view of the full movement jaw advancement oral appliance according to a preferred embodiment of this invention.
Figure 2:
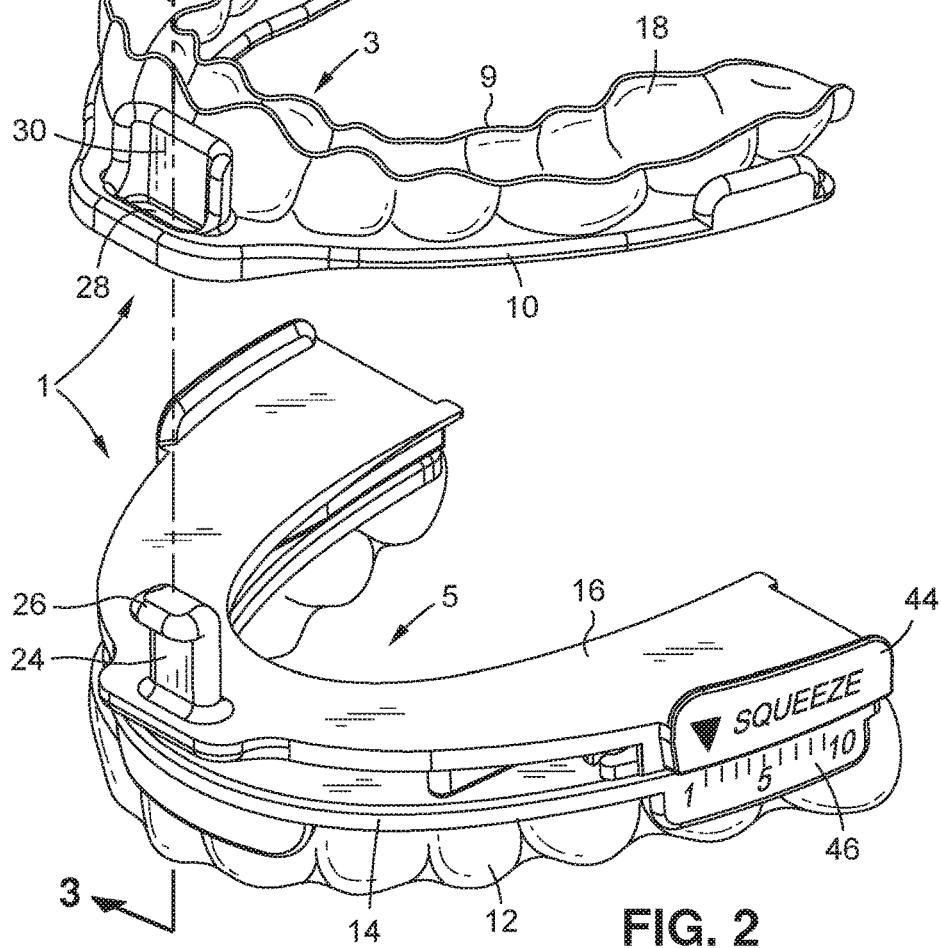
FIG. 2 is an exploded view of the full movement jaw advancement oral appliance of FIG. 1.

Turning to the drawings, details are provided of a full movement jaw advancement oral appliance 1 that is sized to fit within the mouth and over the teeth of a user so that the user's upper jaw can be repositioned in a horizontal direction with respect to his lower jaw by a variable distance that can be selectively and continuously controlled by the user. What is more, and as an important advantage achieved by the oral appliance 1, the user can open his mouth in a vertical direction during sleep without the appliance separating from and becoming misaligned with respect to the user's upper and lower sets of teeth. By virtue of the foregoing, the position of the oral appliance 1 relative to his upper and lower sets of teeth can be manually adjusted by the user without the use of tools, springs, the removal and insertion of fasteners, or the intervention by medical personnel so that a continuous air path through the oral appliance to the user's throat will remain open while the user sleeps. It may therefore be appreciated that the oral appliance 1 has particular application for use during sleep by one wishing to cope with the effects of snoring and/or sleep apnea while reducing the chance that the oral appliance will become separated from and misaligned with respect to the user's teeth should he open his mouth during sleep.

Referring concurrently to FIGS. 1-8 of the drawings, the full movement jaw advancement oral appliance 1 is shown including a flexible upper arch tray assembly 3 and a flexible lower arch tray assembly 5 that are held one above the other to create the aforementioned continuous air path (designated 7 and best shown in FIG. 6) through the oral appliance to the user's throat. As will be disclosed in greater detail hereinafter, the upper and lower arch tray assemblies 3 and 5 are coupled to one another such that the upper assembly 3 can be moved by the user relative to the lower assembly 5 back and forth along a horizontal plane. Likewise, the upper assembly 3 can be moved relative to the lower assembly 5 up and down along a vertical plane.

In the case where the upper arch tray assembly 3 is moved as will be hereinafter described by the user in a horizontal direction, the user's upper jaw is correspondingly displaced relative to his lower jaw to enable the size of the air path 7 through the oral appliance 1 to be selectively adjusted. In the case where the upper arch tray assembly 3 moves upwardly in a vertical direction, such as when the user opens his mouth during sleep, the user's upper set of teeth will move upwardly with the upper arch tray assembly 3 so as to remain in contact and alignment therewith.

Figure 7:
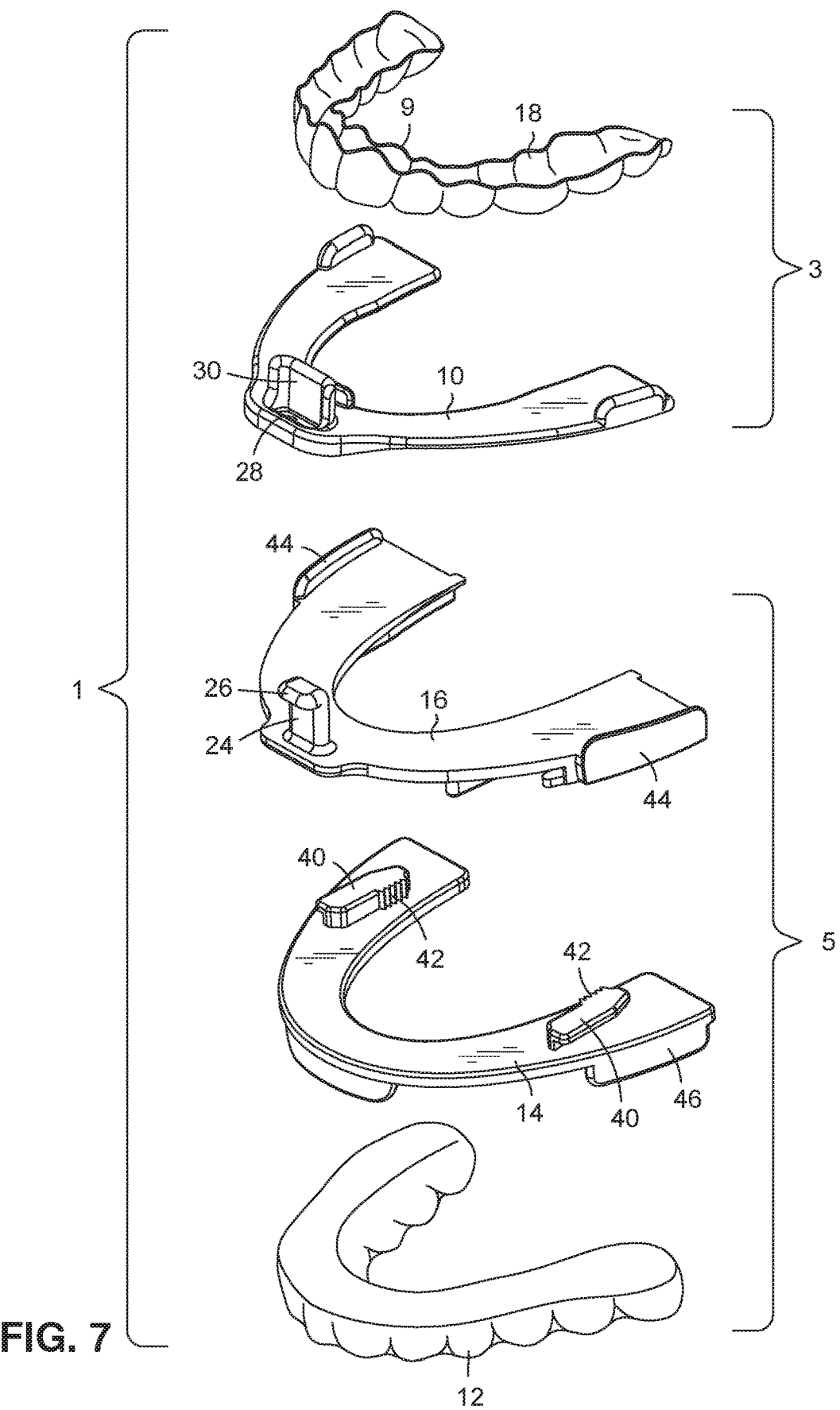
FIG. 7 is an exploded top view of the upper and lower arch tray assemblies of the full movement jaw advancement oral appliance shown in FIG. 6.
Figure 8:
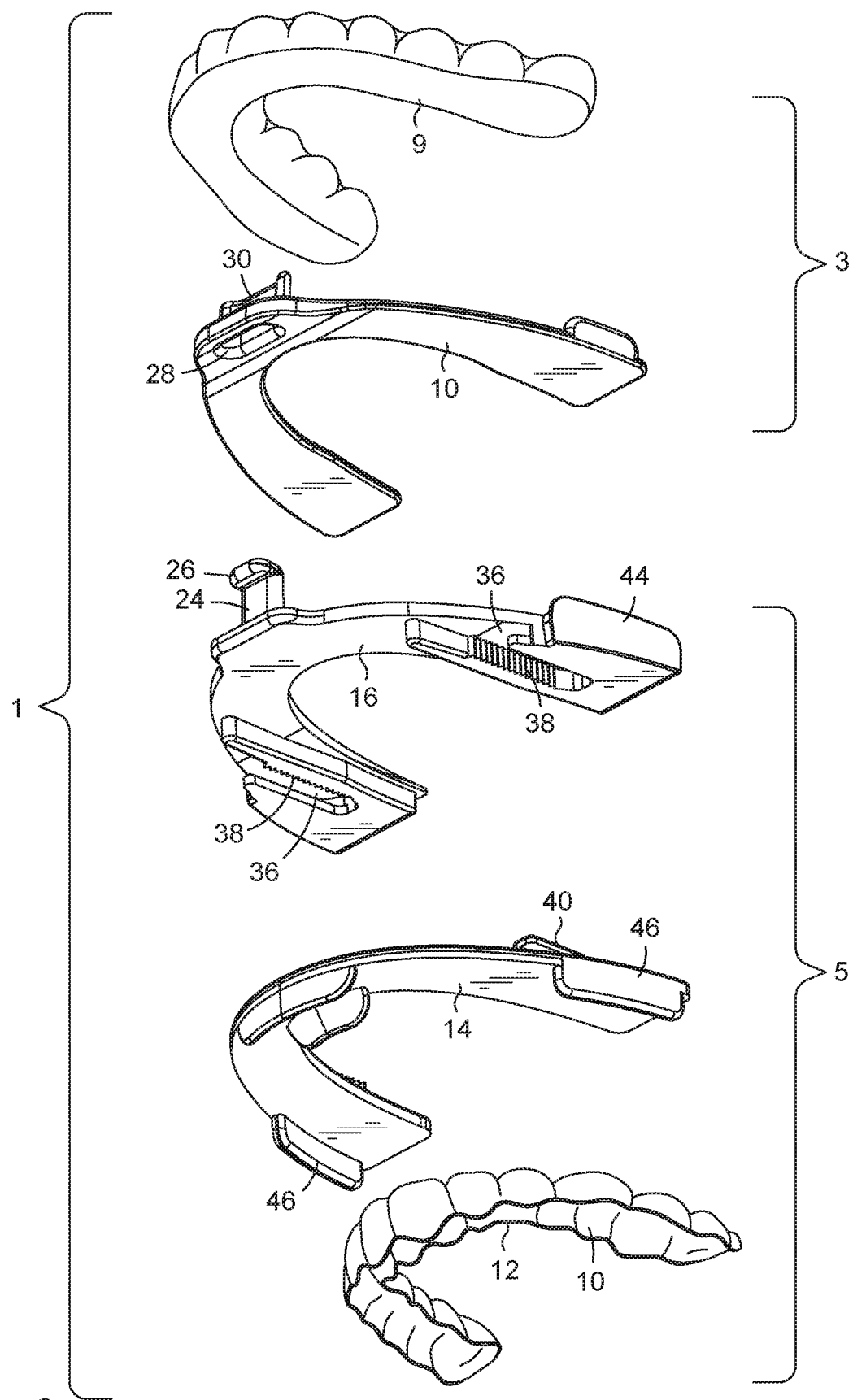
FIG. 8 is an exploded bottom view of the upper and lower arch tray assemblies of the full movement jaw advancement oral appliance shown in FIG. 6.

As is best shown in FIGS. 7 and 8, the upper arch tray assembly 3 of the full movement jaw advancement appliance 1 includes an upper tooth impression liner 9 and an upper liner receiving tray 10 that are bonded together (e.g., by means of a biocompatible glue) so that the tooth impression liner 9 is held in place on top of the liner receiving tray 10. Each of the upper tooth impression liner 9 and the upper liner receiving tray 10 has a generally arcuate configuration to match the bite pattern of the user's teeth carried by his upper jaw. By way of example only, the upper tooth impression tray 9 is manufactured from a relatively soft and impressionable thermal formed plastic or thermal set copolymer plastic, and the upper liner receiving tray 10 is manufactured from a relatively hard polycarbonate.

Continuing to refer to FIGS. 7 and 8, the lower arch tray assembly 5 of the full movement jaw advancement appliance 1 includes a lower tooth impression liner 12 and a lower liner receiving tray 14 that are bonded together so that the liner receiving tray 14 is held in place on top of the lower tooth impression liner 12. As in the case of the upper tooth impression liner 9 and the upper liner receiving tray 10, each of the lower tooth impression liner 12 and the lower liner receiving tray 14 has a generally arcuate configuration to match the bite pattern of the user's teeth carried by his lower jaw. Also like the upper tooth impression liner 9 and the upper liner receiving tray 10, the lower tooth impression liner 12 is ideally manufactured from a relatively soft and impressionable plastic material, and the lower liner receiving tray 14 is manufactured from a relatively hard plastic material.

The lower arch tray assembly 5 also includes a flexible intermediate guide post support tray 16 that is coupled to the lower liner receiving tray 14 in a manner that will soon be described. The intermediate guide post support tray 16 has a generally arcuate configuration to match that of the lower liner receiving tray 14. The guide post support tray 16 is ideally manufactured from a relatively hard plastic (e.g., polycarbonate) to match the material from which the lower liner receiving tray 14 is manufactured.

An upper bite channel 18 (best shown in FIG. 7) runs around the top of the arcuate upper tooth impression liner 9 of the upper arch tray assembly 3. The upper bite channel 18 is sized to receive therewithin the upper set of teeth of the user carried by his upper jaw. Inasmuch as the relatively soft upper tooth impression liner 9 lays over and against the relatively hard upper liner receiving tray 10, a biting force generated by the user's upper set of teeth and applied to the upper tooth impression liner 9 can initially shape the upper bite channel 18 after the oral appliance has first been heated (e.g., in a pot of boiling water) and, following cooling, inserted into the user's mouth.

A lower bite channel 20 (best shown in FIG. 8) runs around the bottom of the arcuate lower tooth impression liner 12 of the lower arch tray assembly 5. The lower bite channel 20 is sized to receive therewithin the lower set of teeth of the user carried by his lower jaw. Inasmuch as the relatively soft lower tooth impression liner 12 lays below and against the relatively hard lower liner receiving tray 14, a biting force generated by the user's lower set of teeth and applied to the lower tooth impression liner 12 can initially shape the lower bite channel 20 at the same time that the upper bite channel 18 from the upper tooth impression liner 9 is being shaped.

As an important feature of the full movement jaw advancement appliance 1, a vertical upper arch tray retaining post 24 stands upwardly from the front of the intermediate guide post support tray 16 of the lower arch tray assembly 5. A stop 26 turns horizontally outward from the top of the retaining post 24. A retaining post receiving opening 28 is formed through the front of upper liner receiving tray 10 of the upper arch tray assembly 3 so as to lie ahead of the upper tooth impression liner 9 that is bonded to tray 10. A retaining post guide 30 stands upwardly from the upper liner receiving tray 10 so as to lie immediately behind the retaining post receiving opening 28.

Figure 3:
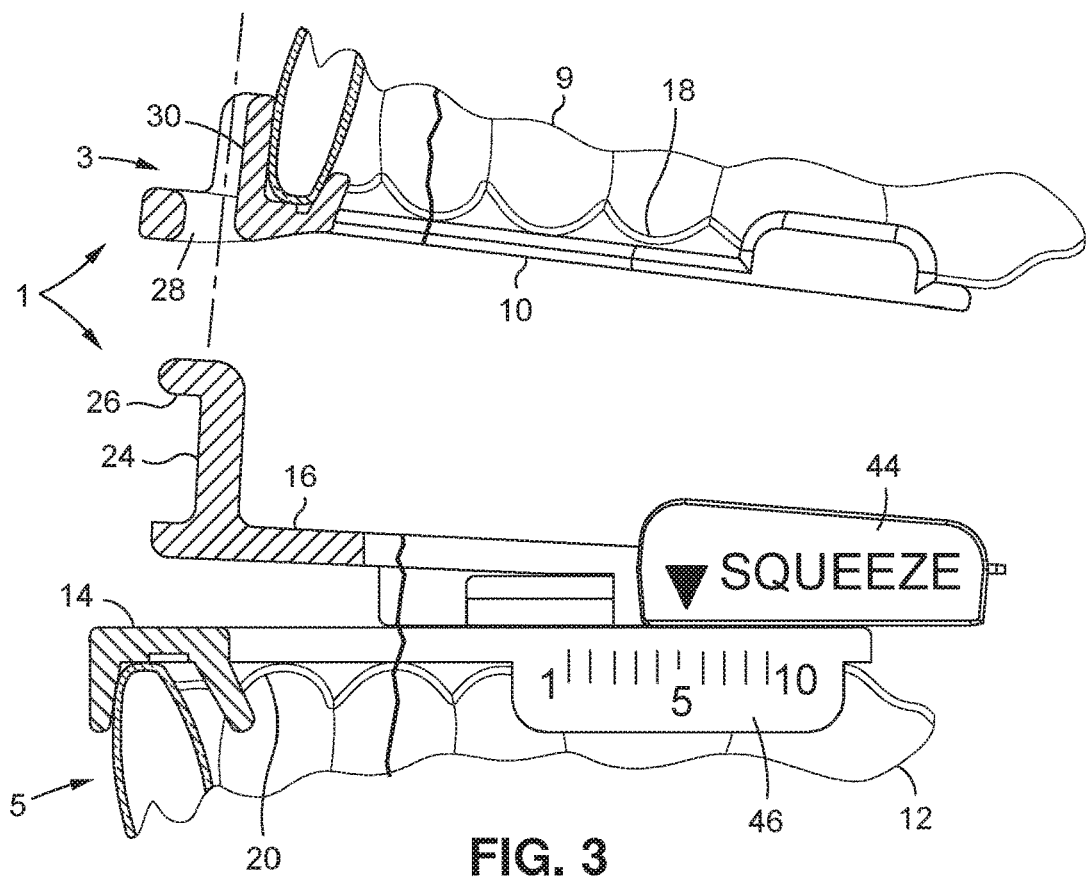
FIG. 3 is a cross-section of the full movement jaw advancement oral appliance taken along lines 3-3 of FIG. 2.
Figure 4:
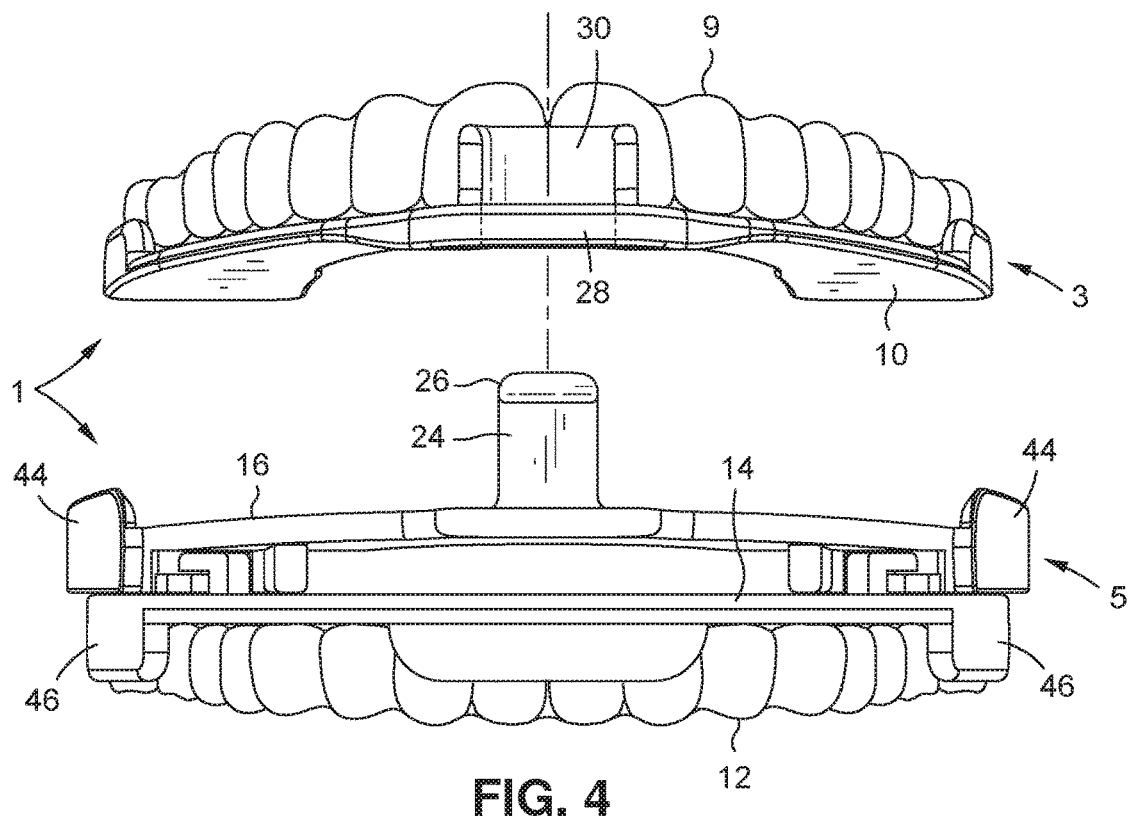
FIG. 4 is an exploded front view of the full movement jaw advancement oral appliance shown in FIG. 2.

As is best shown in FIGS. 3 and 4, the upstanding upper arch tray retaining post 24 of the lower arch tray assembly 5 is axially aligned with the retaining post receiving opening 28 of the upper arch tray assembly 3. The upper and lower arch tray assemblies 3 and 5 are coupled together one above the other when the upper arch tray receiving post 24 is pushed through the post receiving opening 28 so as to ride over and against the upstanding retaining post guide 30 (best shown in FIGS. 1 and 2). The stop 26 extending outwardly from the top of the retaining post 24 prevents the withdrawal of the retaining post 24 from the retaining post receiving opening 28 and a separation of the upper and lower arch tray assemblies 3 and 5 from one another.

Figure 5:
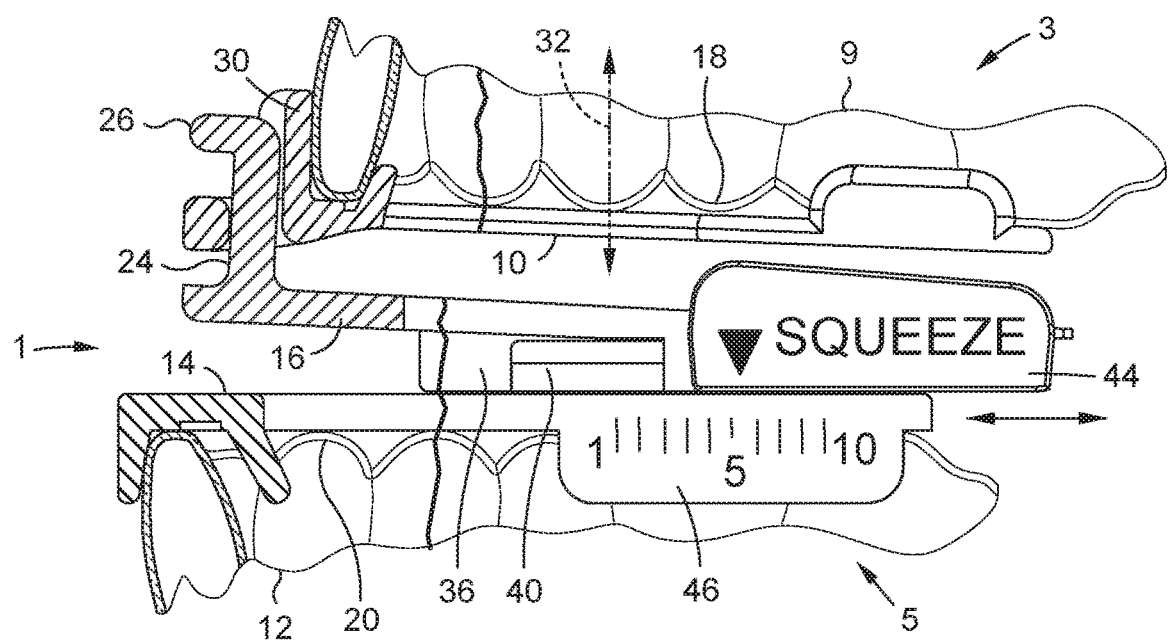
FIG. 5 is a cross-section of the full movement jaw advancement oral appliance of FIG. 4 with upper and lower arch tray assemblies of the oral appliance coupled together and lying one above the other.
Figure 6:
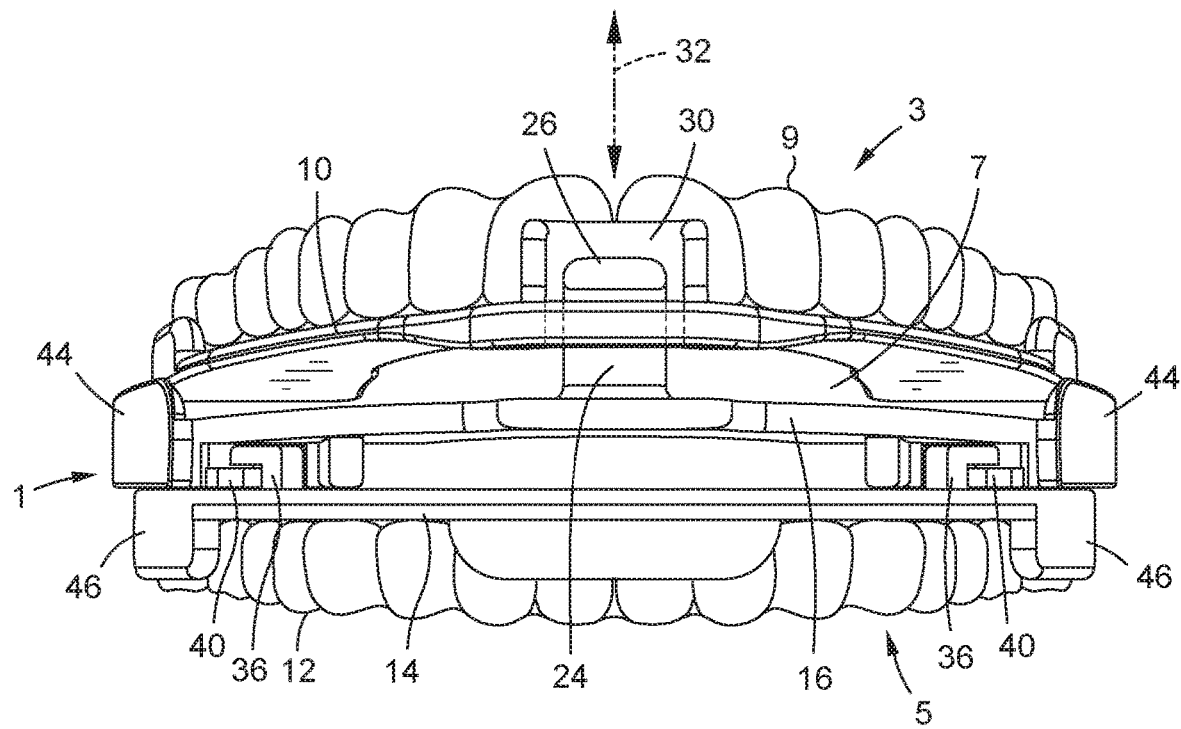
FIG. 6 is a front view of the full movement jaw advancement oral appliance shown in FIG. 5.

It may be appreciated that should the user open and close his mouth with the full movement oral appliance 1 covering his teeth during sleep, the upper liner receiving tray 10 of the upper arch tray assembly 3 will move upwardly and downwardly with the user's upper jaw as indicated by the directional arrows 32 of FIGS. 5 and 6. In this same regard, the user's upper set of teeth will remain in receipt by and alignment with the upper bite channel 18.

That is, when the user lifts his upper jaw during sleep, the upper arch tray assembly 3 will be correspondingly lifted so as to travel upwardly along the upper arch tray retaining post 24 which stands upwardly from the intermediate guide post support tray 16 of the lower arch tray assembly 5. The upper arch tray assembly 3 will continue to be lifted above the lower arch tray assembly 5 until the stop 26 at the top of the upper arch tray retaining post 24 engages the opening 28 at the front of the upper liner receiving tray 10. The important advantage achieved by the aforementioned upward movement of the upper arch tray assembly 3 above the lower arch tray assembly 5 is that the user's upper set of teeth will not separate from the upper bite channel 18 of the upper tooth impression liner 9 which might cause the oral appliance to be undesirably repositioned in the user's mouth as his upper jaw is repeatedly opened throughout the night.

Referring specifically to FIG. 8, a recessed locking channel 36 is shown formed (e.g., molded) into the bottom and at each side of the arcuate intermediate guide post support tray 16 of the lower arch tray assembly 5 of the full movement oral appliance 1. The locking channels 36 run parallel to one another. A row of teeth 38 is formed (e.g., molded) along one side of each locking channel 36. As is best shown in FIG. 7, located at opposite sides of and standing upwardly from the arcuate lower liner receiving tray 14 of the lower arch tray assembly 5 of oral appliance 1 are a pair of position adjustment blocks 40. A row of teeth 42 is formed (e.g., molded) along one side of each position control block 40.

During the assembly of the full movement jaw advancement oral appliance 1, the lower arch tray assembly 5 is completed when the lower liner receiving tray 14 is mounted against the bottom of the intermediate guide post support tray 16. To accomplish the foregoing, the pair of position adjustment blocks 40 which stand upwardly from the lower liner receiving tray 14 are pushing into slidable receipt by respective ones of the pair of locking channels 36 that are formed in the bottom of the intermediate guide post support tray 16, whereby the opposing trays 14 and 16 of the lower arch tray assembly 5 are coupled together and held in place one over the other. In this same regard, the rows of teeth 42 which run along one side of the pair of upstanding position adjustment blocks 40 are moved into releasable locking engagement with and mesh against the rows of teeth 38 which run along one side of the pair of recessed locking channels 36. However, it may be appreciated that any suitable interlocking ratchet means may be substituted for the opposing rows of teeth 38 and 42.

By virtue of the foregoing, the user is provided with the ability to release the locking meshing engagement of the teeth 42 of the position adjustment blocks 40 with the teeth 38 of the locking channels 36. Accordingly, and as illustrated in FIG. 5, the position of the lower intermediate guide post support tray 16 of the lower arch tray assembly 5 of the full movement jaw advancement oral appliance 1 can be selectively changed along a horizontal direction relative to the lower liner receiving tray 14 and the lower tooth impression liner 12 of the lower arch tray assembly 5 at which the user's lower set of teeth will be received.

A pair of position control pads 44 are located at and molded into opposite sides of the intermediate guide post support tray 16 of the lower arch tray assembly 5. A position indication scale 46 is molded into or printed onto each side of the lower liner receiving tray 14 of the lower arch tray assembly 5 so as to lie below a position control pad 44. The flexible guide post support tray 16 of the lower arch tray assembly 5 is responsive to momentary compressive squeezing forces simultaneously applied in opposite directions towards one another at the position control pads 44 thereof to temporarily compress and change the shape of the guide post support tray 16, whereby the opposite sides of the support tray 16 are squeezed towards one another. At the same time, the teeth 38 of the locking channels 36 of the guide post support tray 16 are temporarily moved out of their former locking engagement with the teeth 42 of the position adjustment blocks 40 of the lower liner receiving tray 14.

As is best shown in FIG. 5, the user can now apply a pushing (or pulling) force to relocate and change the position of the intermediate guide post support tray 16 of the lower arch tray assembly 5 relative to the lower liner receiving tray 14 and the position indicator scale 46 thereof. Because the intermediate guide post support tray 16 is coupled to the upper liner receiving tray 10 of the upper arch tray assembly 3 by means of the upper arch tray retaining post 24 being received through the retaining post receiving opening 28, both of the upper liner receiving tray 10 and the upper tooth impression liner 9 of the upper arch tray assembly 3 at which the user's upper set of teeth are received will now travel back and forth with one another along with the guide post support tray 16. By changing the position of the upper arch tray assembly 3 in a horizontal direction relative to the lower arch tray assembly 5, the position of the user's upper jaw is correspondingly moved forwards or backwards relative to his lower jaw to change the size of the airway to his throat as may be necessary over time.

When the position of the upper arch tray assembly 3 has been adjusted relative to the position of the lower arch tray assembly 5, the momentary compressive squeezing forces are terminated. Accordingly, the formerly compressed intermediate guide post support tray 16 will automatically expand back to its initial arcuate shape. At the same time, the teeth 38 of the locking channels 36 will move back into their mating interlocking engagement with the opposing teeth 42 of the position adjustment blocks 40 so that the upper and lower arch tray assemblies 3 and 5 will once again be held in place one above the other. The location of the position control pads 44 above the position indication scales 46 provides the user with a visual indication of the position of the upper arch tray assembly 3 with respect to the lower arch tray assembly 5 so that the user can make regular controllable and precise vertical position adjustments of the upper arch tray assembly 3 to correspondingly change the position of his upper jaw relative to his lower jaw.

It has been described herein that the upper arch tray assembly 3 is moved in a vertical direction relative to the lower arch tray assembly 5 once compressive squeezing forces have been applied to the position control pads 44 at opposite sides of the intermediate guide post support tray 16. However, it is to be expressly understood that the lower arch tray assembly 5 can be grasped and moved in the same vertical direction relative to the upper arch tray assembly 3 after the intermediate guide post support tray 16 is first compressed. In this case, the user's lower jaw will be positioned forwards and backwards relative to his upper jaw.

The invention claimed is:

1. A full movement jaw advancement oral appliance to be inserted in the mouth of a user to adjust the position of one of the user's upper or lower jaws relative to the other one of his jaws so as to maintain an open airway through which the user can breathe while sleeping, said oral appliance having a longitudinal axis and comprising:

an upper arch tray assembly having a U-shaped upper liner receiving tray, an upper tooth impression liner laying on said upper liner receiving tray and adapted to receive the upper teeth of the user's upper jaw thereagainst during sleep, and a post receiving opening formed through said upper liner receiving tray; and a lower arch tray assembly having a U-shaped lower liner receiving tray and a lower tooth impression liner laying on said U-shaped lower liner receiving tray and adapted to receive the lower teeth of the user's lower jaw thereagainst during sleep, said lower arch tray assembly also having a U-shaped intermediate guide post support tray including a top and a bottom and an upper arch tray assembly retaining post connected to and standing upwardly from the top of said intermediate guide post support tray for receipt through the post receiving opening formed through the upper liner receiving tray of said upper arch tray assembly, the bottom of said U-shaped intermediate guide post support tray being coupled to the U-shaped lower liner receiving tray of said lower arch tray assembly such that said upper and lower arch tray assemblies are coupled to one another with said U-shaped intermediate guide post support tray lying therebetweew, said intermediate guide post support tray and said upper arch tray assembly moving back and forth with one another in a horizontal direction along the longitudinal axis of said oral appliance relative to the lower liner receiving tray of said lower arch tray assembly to correspondingly adjust the position of the user's upper jaw relative to his lower jaw, and said upper arch tray assembly moving upwardly and downwardly in a vertical direction that runs perpendicular to said horizontal direction so as to slide along said upper arch tray assembly retaining post relative to said lower arch tray assembly and said intermediate guide post support tray thereof whereby the upper tooth impression liner of said upper arch tray assembly will remain in receipt of the user's upper teeth when he opens his mouth during sleep.

2. The full movement jaw advancement oral appliance recited in claim 1, wherein there is a retaining post guide standing upwardly from the upper liner receiving tray of said upper arch tray assembly adjacent said post receiving opening formed therethrough, said upper arch tray assembly retaining post sliding along said retaining post guide when said upper arch tray assembly moves upwardly and downwardly in said vertical direction relative to said lower arch tray assembly and said intermediate guide post support tray thereof.

3. The full movement jaw advancement oral appliance recited in claim 1, wherein there is a stop extending from said upper arch tray assembly retaining post so as to prevent the separation of said upper arch tray assembly retaining post from its receipt said retaining post receiving opening and thereby prevent said upper arch tray assembly and said lower arch tray assembly front being uncoupled.

4. The full movement jaw advancement oral appliance recited in claim 1, wherein each of said U-shaped intermediate guide post support tray and the U-shaped lower liner receiving tray of said lower arch tray assembly has an arcuate shape with a front and a pair of sides that are spaced from and lie opposite one another, one of said arcuate intermediate guide post support tray or said arcuate lower liner receiving tray having a position adjustment block located at each of the pair of sides thereof and the other one of said arcuate intermediate guide post support tray or said arcuate lower liner receiving tray having a locking channel located at each of the pair of sides thereof, each position adjustment block being received within and slidable through a respective locking channel when said intermediate guide post support tray and said upper arch tray assembly move back and forth with one another in said horizontal direction relative to the lower liner receiving tray of said lower arch tray assembly.

5. The full movement jaw advancement oral appliance recited in claim 4, wherein each position adjustment block and each locking channel located at each of the sides of said arcuate intermediate guide post support tray and said arcuate lower liner receiving tray of said lower arch tray assembly has a set of teeth, the sets of teeth of said position adjustment blocks and said locking channels lying in meshing engagement with one another, whereby said intermediate guide post support tray and said lower liner receiving tray are mated in releasable locking engagement with one another.

6. The full movement jaw advancement oral appliance recited in claim 5, wherein said arcuate intermediate guide post support tray is responsive to compressive forces being simultaneously applied in opposite directions to the pair of sides thereof to compress said arcuate intermediate guide post support tray and thereby move the sets of teeth of said locking channels out of their meshing engagement with the sets of teeth of the position adjustment blocks to enable said locking channels to slide past said position control blocks and said intermediate guide post support tray and said upper arch tray assembly to move back and forth with one another in said horizontal direction relative to said lower liner receiving tray of said lower arch tray assembly.

\* \* \* \* \*